US 6,481,569 B1

(12) United States Patent
Alpern

(10) Patent No.: US 6,481,569 B1
(45) Date of Patent: Nov. 19, 2002

(54) NEEDLE PARK AND METHOD OF USE

(75) Inventor: Marvin Alpern, Glen Ridge, NJ (US)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 09/648,801

(22) Filed: Aug. 28, 2000

Related U.S. Application Data

(63) Continuation of application No. 09/266,539, filed on Mar. 11, 1999, now abandoned.

(51) Int. Cl.$^7$ ............................................. A61B 17/06
(52) U.S. Cl. ..................................... 206/63.3; 206/380
(58) Field of Search ....................... 206/63.3, 380–382, 206/339, 480, 482; 53/425, 430

(56) References Cited

U.S. PATENT DOCUMENTS

| | | |
|---|---|---|
| 4,424,898 A | 1/1984 | Thyen et al. |
| 4,961,498 A | 10/1990 | Kalinski et al. |
| 4,967,902 A | 11/1990 | Sobel et al. |
| 5,052,551 A | 10/1991 | Cerwin et al. |
| 5,056,658 A | 10/1991 | Sobel et al. |
| 5,099,994 A * | 3/1992 | Kalinski et al. ........... 206/63.3 |
| 5,131,533 A * | 7/1992 | Alpern ....................... 206/63.3 |
| 5,180,053 A | 1/1993 | Cascio et al. |
| 5,192,483 A | 3/1993 | Kilgrow et al. |
| 5,230,424 A * | 7/1993 | Alpern et al. ............... 206/63.3 |
| 5,350,060 A * | 9/1994 | Alpern et al. ............... 206/63.3 |
| 5,472,081 A | 12/1995 | Kilgrow et al. |
| 5,733,293 A * | 3/1998 | Scirica et al. .............. 206/63.3 |
| 5,833,055 A * | 11/1998 | Cerwin et al. ............. 206/63.3 |
| 6,135,272 A * | 10/2000 | Sobel et al. ............... 206/63.3 |

* cited by examiner

Primary Examiner—Luan K. Bui

(57) ABSTRACT

A needle park and method of use of same, wherein a two-point contact, cantilevered member and opposite post member are provided to hold a needle between them, the post member being slit partially, such as perpendicular to or parallel to, the base on which the park sits. Such a slit allows the post member to partially collapse when a needle is inserted, allowing a greater variety of needle diameters to be used. Any curved needle is inserted in the separation between the members so that the needle curves around the post member and away from the two-point contact member.

10 Claims, 4 Drawing Sheets

NEEDLE PARK AND METHOD OF USE

This is a Continuation of prior application Ser. No. 09/266,539, filed Mar. 11, 1999 now abandoned.

FIELD OF THE INVENTION

This invention relates to a needle park for needles such as suture needles, particularly a park which can hold in the same location a variety of diameters of needles.

BACKGROUND OF THE INVENTION

It is well-known to provide a molded three-point contact needle park for surgical and suture needles. Such parks have also been constructed so that the same park can accommodate a variety of diameters of the needles. Particularly useful examples of these are described in commonly-owned U.S. Pat. No. 5,131,533. The park in such examples comprises: a base; a two-point contact member cantilevered upwardly over the base, the member being generally curved with a concave curve and terminating in two vertically-extending outboard corners; and a solid post member extending upwardly from the base and positioned in-between the corners, the post having a contact end with a separation from the concave curve of the two-point contact member that is effective to receive and grip a needle between the contact end and the corners. When used with curved needles, the needle is positioned so as to curve away from the post member and around the two outboard corners, FIGS. 3 and 4 of said '533 patent.

Although such a needle park has been very successful and allows for the parking of a variety of needle diameters in the same park, that variety has been less than universal. Thus, the typical diameters accommodated by that needle park has ranged from 0.3 mm (0.012 inch) to 1.0 mm (0.039 inch). That is, it has not been useful also for needles of diameters of 0.2 mm (0.008 inch), 0.254 mm (0.010 inch) and 1.12 or 1.27 mm (0.044 or 0.050 inch), all of which are conventional sizes.

Furthermore, certain needles known as cutting edge needles are edged along their length so as to provide a cutting action. To this end, the needle is generally triangular in transverse cross-section, at least at the portion fitting within the needle park. It can be shown that, with such a triangular cross-section positioned in a three-point contact park, the post contact in-between the two outboard contacts will prevail, as against the outboard contacts, regarding the direction of pivot of the triangle and hence of the curved needle. That is, when the curved needle is positioned to curve away from the in-between post contact, as in the '533 patent, the effect is to cause the triangle to rotate outwardly and up from the post contact, that is, to cause the ends of the needle to pivot away from the base of the park. Because one of those ends is pointed and very sharp, this can create a needle-prick hazard to any unwary user of the needle park. It can also cause a needle end to prematurely puncture any sterile wrapping, compromising the sterility.

Thus, prior to this invention, there has been a need to provide a needle park that will both accommodate a greater variety of sizes of needles, and, when used with a curved cutting edge needle, will ensure that the ends of such curved needle remain flat against the base of the park away from free encounter with the skin of a user or of any wrapping.

SUMMARY OF THE INVENTION

I have constructed a needle park which solves the aforementioned need.

More specifically, in accord with one aspect of the invention, there is provided a needle park for securing a needle, the park comprising: a base; a two-point contact member cantilevered upwardly over the base, the member being generally curved with a concave curve and terminating in two vertically-extending outboard corners; and a post member extending upwardly from the base and positioned in-between the corners, the post having a contact end with a separation from the concave curve of the two-point contact member that is effective to receive and grip a needle between the contact end and the corners, the post member further including a collapsible slit extending at least partway into the post member from the contact end; so that a wide range of diameters of needles can be forced to fit between the members of the needle park, by collapsing the post end at the slit when any one of the needles is forced to fit in said separation.

In accord with another aspect of the invention, there is provided a needle park for securing a needle, the park comprising: a base; a two-point contact member cantilevered upwardly over the base, the member being generally curved with a concave curve and terminating in two vertically-extending outboard corners; and a post member extending upwardly from the base and positioned in-between the corners, the post having a contact end with a separation from the concave curve of the two-point contact member that is effective to receive and grip a needle between the contact end and the corners; and a curved needle fitted and held between the members, the needle being curved around the post member and away from the two-point curved contact member, so that the curved needle is biased downwardly towards the base.

In accord with still another aspect of the invention, there is provided a method of safely mounting a curved cutting edge needle in a needle park, the park comprising: a base; a two-point contact member cantilevered upwardly over the base, the member being general curved with a concave and terminating in two vertically-extending outboard corners; and a post member extending upwardly from the base and positioned in-between the corners, the post having a contact end with a separation from the concave curve of the two-point contact member that is effective to receive and grip a needle between the contact end and the corners; the method comprising the step of positioning a curved cutting edge needle above the separation and generally horizontal to the base, so that the needle curves around the post member and away from the two-point curved contact member; and forcing the needle to be gripped between the members by pushing the needle so positioned down into said separation causing at least the cantilevered two-point contact member to pivot out of the way of the needle.

Accordingly, it is an advantageous feature of the invention that a greater variety of needle diameters can be accommodated within the same needle park.

It is another advantageous feature of the invention that such a needle park can be used to safely mount a cutting edge needle to ensure that its ends, and particularly the sharp pointed end, remain pivoted down against the base of the needle park, and out of harm's way.

Other advantageous features will become apparent upon reference to the following Detailed Description, in light of the attached drawings.

DESCRIPTION OF THE PREFERRED EMBODIMENTS

The invention is described in connection with certain preferred embodiments, wherein the needle park is provided in a package having a tray construction which preferably is similar to those described in commonly owned U.S. application Ser. No. 09/143,818 filed Aug. 31, 1998 by Sobel et al U.S. Pat. No. 6,047,815, entitled "Package for Sutures", Attorney Doc. Eth-1326, or those described in U.S. Pat. No. 5,131,533. In addition, the invention is useful regardless of the construction of the tray that the needle park is located in, and regardless of the type of needle used with the needle suture or the type of suture, so long as there is in fact a park for a needle. For example, the needle park can also be used in the tray described in U.S. Pat. No. 5,833,055.

Figure 1:
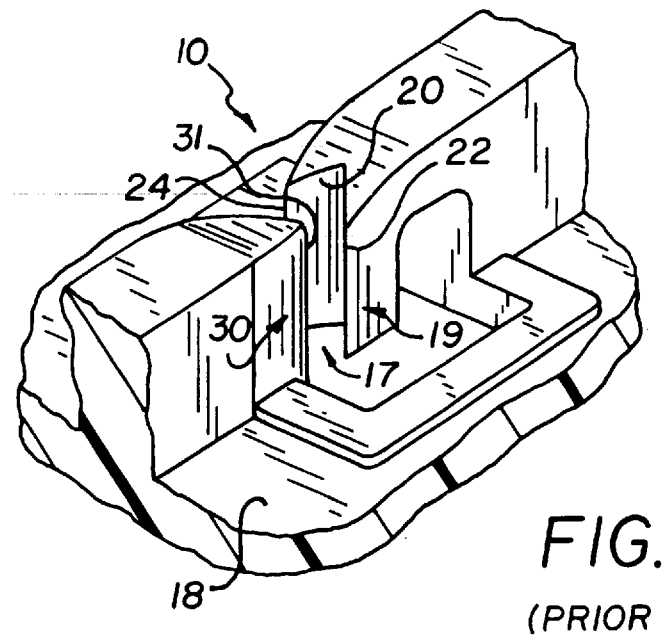
FIG. 1 is a fragmentary perspective view of a needle park constructed in accordance with the prior art.
Figure 2:
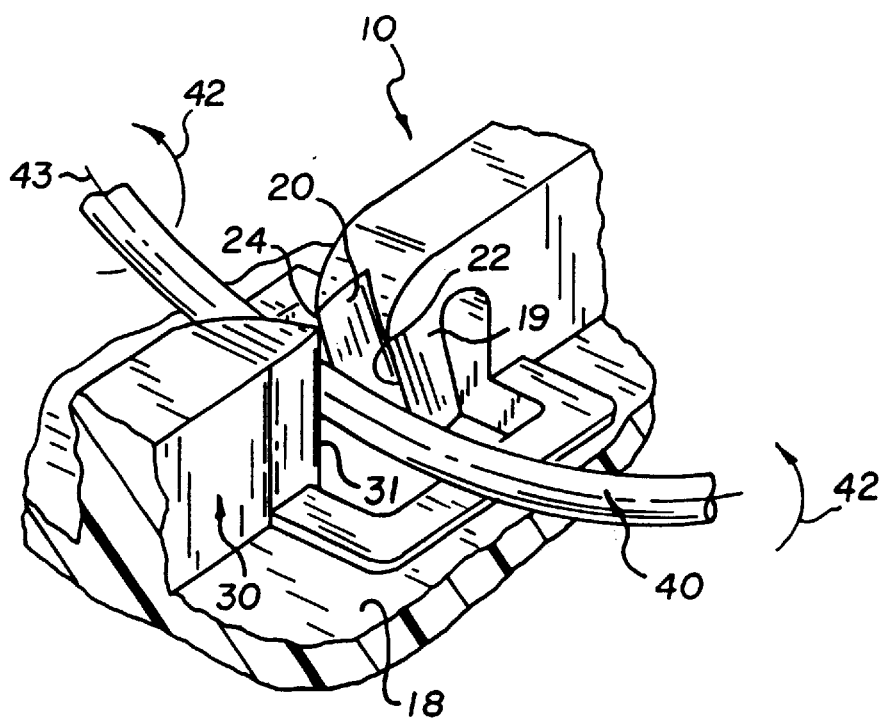
FIG. 2 is a perspective view similar to FIG. 1, of the needle park with a needle in place.

FIGS. 1 and 2 illustrate the needle park 10 of the aforesaid '533 patent. That is, a base 18 has an opening 17 formed therein, and a two-point contact member 19 cantilevered out from base 18, into opening 17. Member 19 has a concave curve 20 forming a needle-contact surface, such surface terminating in two vertically extending (when in use) corners 22 and 24.

Opposite to member 19 is post member 30, slightly cantilevered out from base 18 into opening 17. Member 30 terminates in a contact end 31 extending generally parallel to and between, corners 22 and 24. The spacing between end 31 and curved surface 20 is effective to receive and grip a needle 40 of a needled suture, FIG. 2, between members 19 and 30. Such needle is mounted so that it curves around the two-point contact member 19, and not post member 30. The two points of contact occur, of course, from vertical corners 22 and 24.

An unfortunate result of the construction shown in FIG. 2, at least if used with a cutting edge needle (not shown), is that post 30 by pressing between contacts 22 and 24, causes needle 40 to pivot, arrows 42, about its axis of symmetry 43, forcing the two needle ends (not shown) to rise off base 18, as described in more detail hereinafter.

Figure 4:
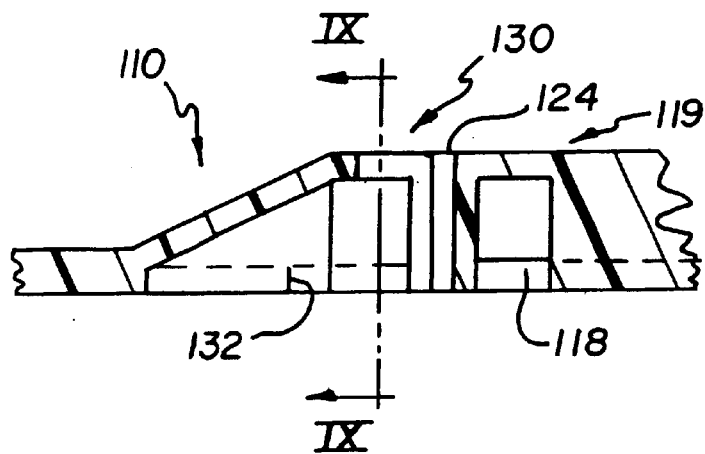
FIG. 4 is a fragmentary section view taken along the plane IV—IV of FIG. 3.
Figure 5:
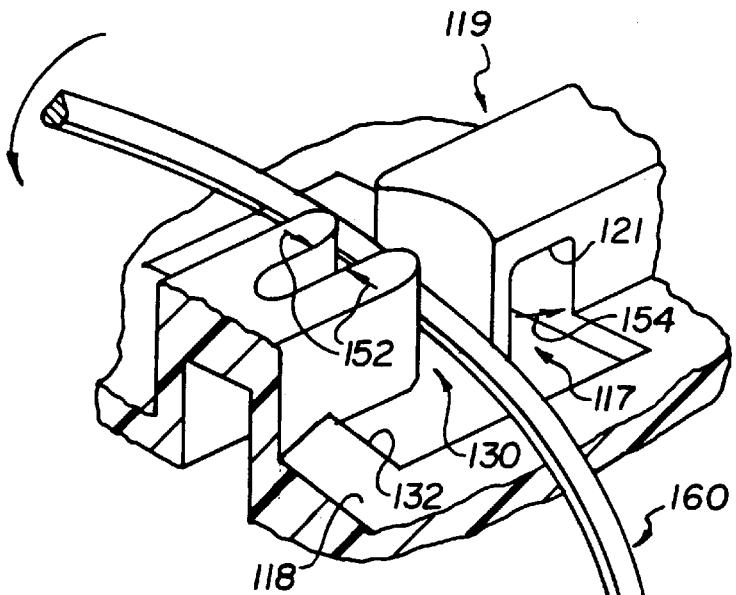
FIG. 5 is a fragmentary perspective view of the needle park similar to that of FIG. 3, but showing a needle in place.

In accordance with the invention, FIGS. 3–5, such a needle park is improved as follows: Parts similar to those of the prior art shown in FIGS. 1 and 2 bear the same reference numeral, to which "100" has been added.

Figure 3:
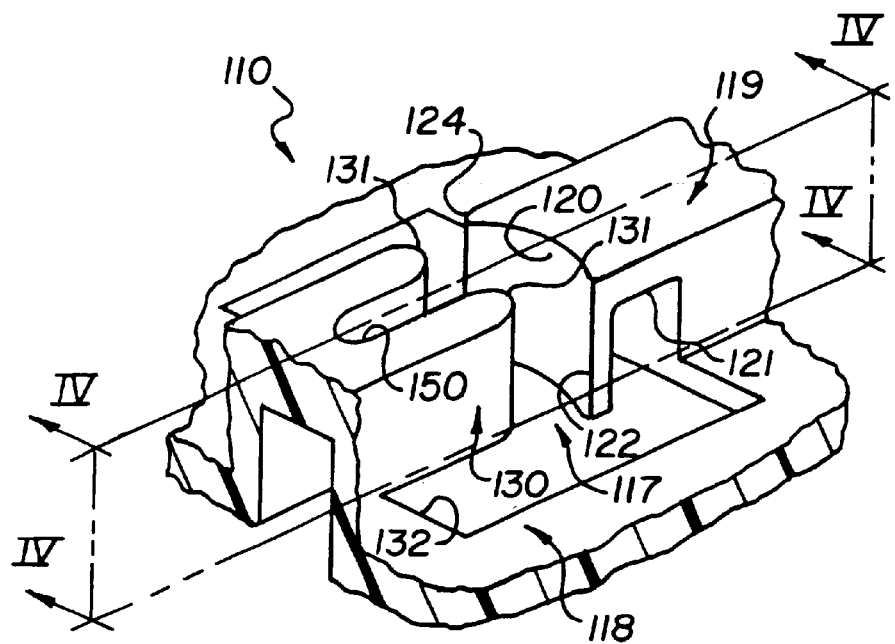
FIG. 3 is a fragmentary perspective view of the needle park constructed in accord with the invention.

Thus, FIG. 3, needle park 110 comprises a base 118 in which an opening 117 is provided. A two-point contact member 119 is cantilevered as an overhanging lip from base 118, into opening 117. Cut-out 121 forms the overhang similar to the prior art construction. Member 119 has a concave curve 120 forming a needle-contact surface, that surface terminating in two vertically extending (when in use) corners 122 and 124. Opposite to member 119 is a post member 130, also cantilevered out from base 118 into opening 117. The cantilever of member 130 is due to its extension beyond vertical face 132 defining the extent of opening 117, FIGS. 3 and 4. Member 130 terminates in a contact end surface 131 extending generally parallel to, and between, corners 122 and 124. Unlike the '533 patent, contact end 131 is improved in that a collapsible slit 150 is formed therein, extending partway into post member 130. This slit allows post member 130 to collapse partially upon itself, arrows 152, FIG. 5. when a needle 160 is inserted between members 119 and 130. Contact member 119 is also forced into cut-out 121 slightly, arrow 154. It is the partial collapse arrows 152, and inward turn of contact member 119, arrow 154, that allow needle park 110 to receive a wide variety of sizes of needles, including diameters of 0.2 mm all the way up to 1.27 mm.

Figure 9:
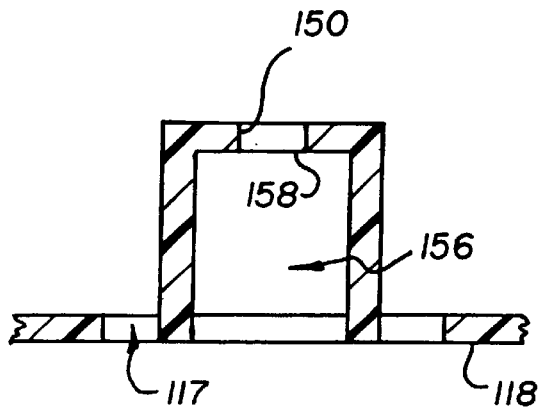
FIG. 9 is a cross-sectional view, taken along section line IX—IX and looking in the direction of the arrows, of the needle park shown in FIG. 4.

Post member 130 can be solid except for slit 150. Preferably, however, it is hollow as shown, with an undercut 156 that forms a roof 158, FIGS. 3–5. As shown better in FIG. 9, the under-cut extends even to the portion of the post member 130 in which slit 150 is formed. The advantage of this construction is that it more readily allows the partial collapse of member 130 shown by arrows 152, than would be the case for a solid member 130.

Yet another improvement is provided in the manner in which a needle (with or without a suture) is inserted into this park 100. That is, needle 160, shown here as a cutting edge needle, is inserted from above the park, so that the needle curves around post member 130, FIG. 5, and away from the two-contact member 119, contrary to the prior art construction, as the needle is pushed into place between members 119 and 130. This is particularly significant when needle 160 is a cutting edge needle, as shown, having a triangular cross-section.

Figure 7:
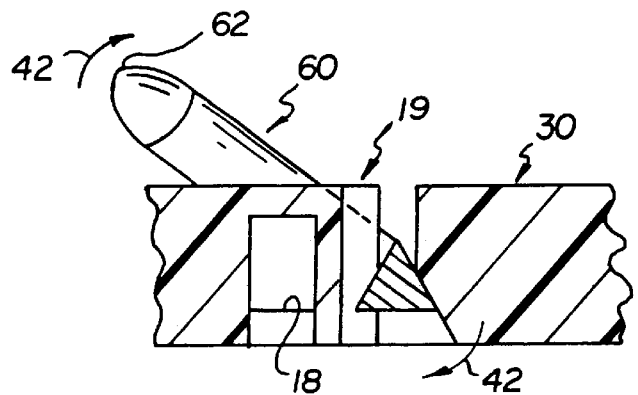
FIG. 7 is a vertical section view of a needle park of the prior art, showing a cutting edge needle in place and unfortunately pivoted outwardly.
Figure 8:
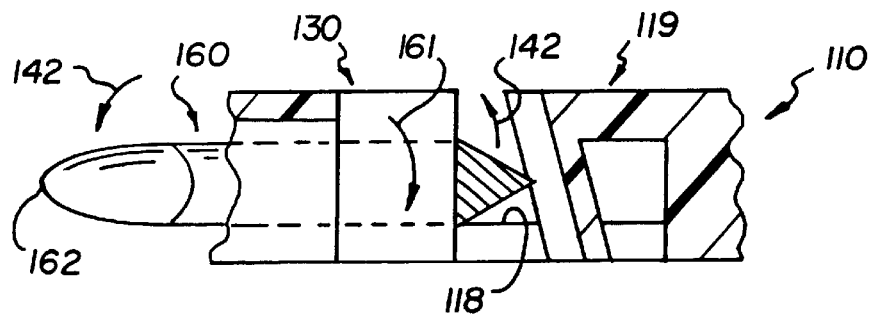
FIG. 8 is the same view as in FIG. 7, but of the needle park of the invention.

This is more clearly demonstrated in FIGS. 7 and 8. In the prior art construction of FIGS. 1 and 2, a cutting edge needle 60 is forced by post member 30, to pivot its ends 62 upwardly arrow 42, causing the point of end 62 to endanger a user or any sterility wrapping applied to the tray. But because needle 60 is curved cutting edge needle 160 to pivot, arrows 142, so that end-point 162 lies flat on the tray, out of danger.

The rest of the tray with which needle park 110 is used, is not shown, as that is conventional. It can comprise any one of a number of trays as noted above.

Figure 6A:
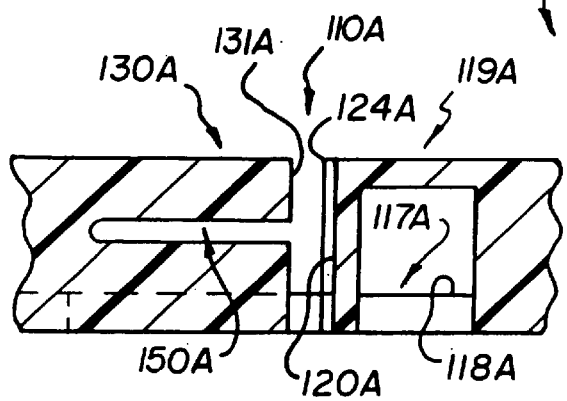
FIG. 6A is a section view similar to that of FIG. 4, but of an alternative embodiment and without the needle.
Figure 6B:
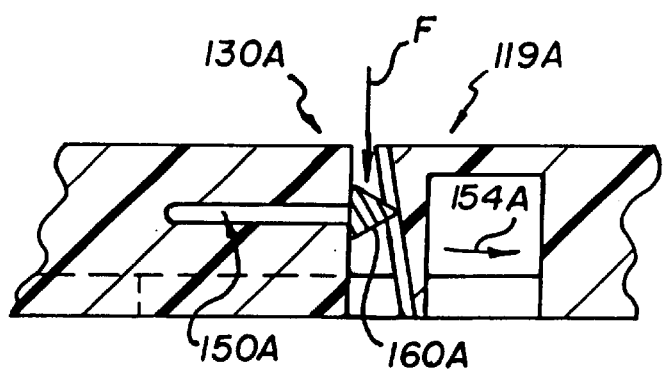
FIG. 6B is a view identical to that of FIG. 6A but with the needle forced into position in the park.

It is not necessary that the slit in the post member extend generally perpendicular to the base and parallel to the outboard corners of the two-point contact member, that is, generally vertically when used. Instead, FIGS. 6A and 6B, the slit can extend generally perpendicularly to those outboard corners and generally parallel to the base. Parts similar to those previously described bear the same reference numeral, to which the distinguishing suffix "A" is appended. Thus, park 110A has a two-point contact member 119A with a concave surface 120A terminating in two vertically-extending (when in use) outboard corners (only 124A being shown), the member being cantilevered from base 118A into opening 117A, as in the previous embodiment. Opposite member 119A is post number 130A, also cantilevered from base 118A, again as describe above, with contact end 131A projecting between corners 122A and 124A of the opposite member. However, FIG. 6A, unlike the previous embodiment, slit 150A which extends partway into member 130A, extends generally parallel to base 118A and perpendicularly to corners 122A and 124B. Its function, however, is similar—it allows member 130A to partially collapse, FIG. 6B, when a needle, such as a cutting edge needle 160A, is forced into the park, arrow F, in the separation between members 119A and 130A. As before, needle 160A is pushed into place so that the curve of the needle curves it around post member 130A and away from two-point contact member 119A.

The partial collapse of slit 150A, along with the inward swing, arrow 154A, of member 119A, allows for a wider variety of sizes of needles to fit in the separation, than in the prior art construction.

The invention disclosed herein may be practiced in the absence of any element which is not specifically disclosed herein.

The invention has been described in detail with particular reference to preferred embodiments thereof, but it will be understood that variations and modifications can be effected within the spirit and scope of the invention.

What is claimed is:

1. A needle park for securing a needle, said needle park comprising:

a base having an opening therein;

a two-point contact member positioned on one side of said opening and cantilevered out from said base over said opening, said contact member having two outboard corners and a generally curved surface which is concave relative to an opposite side of said opening and which is positioned between said corners; and a generally U-shaped post member positioned on said opposite side of said opening and cantilevered out from said base over said opening, said post member having a pair of spaced-apart legs extending outwardly from said post member toward said contact member, each of said legs having a free end terminating a distance from said contact member, thereby creating a space between said post member and said contact member, said space being sized and shaped to receive a needle, said legs being deflectable toward each other in response to a needle being inserted into said space, whereby a wide range of needles having different diameters can be received in said space.

2. A needle park as defined in claim 1, wherein said post member includes a slit between said legs, said slit extending generally perpendicularly to said base.

3. A needle park as defined in claim 1, wherein said post member includes a slit between said legs, said slit extending generally parallel to said base.

4. A needle park as defined in claim 1, wherein said contact member cooperates with said post member so as to orient a curved needle inserted into said space such that its curvature is complementary to that of said curved surface of said contact member.

5. A needle park as defined in claim 4, wherein said contact member cooperates with said post member such that a cutting edge needle having a generally triangular cross-section is pivoted downward towards said base to avoid being a needle-prick hazard.

6. A needle park as defined in claim 1, wherein said post member is hollow.

7. A needle park as defined in claim 1, wherein said legs of said post member are positioned such that one of said legs is alongside the other of said legs.

8. A needle park as defined in claim 7, wherein said one leg extends toward one of said corners of said contact member and said other leg extends toward the other of said corners of said contact member.

9. A needle park as defined in claim 1, wherein said legs of said post member are positioned such that one of said legs is above the other of said legs.

10. A needle park as defined in claim 1, wherein said post member is solid.

* * * * *